United States Patent
Beard et al.

(10) Patent No.: US 6,759,547 B1
(45) Date of Patent: Jul. 6, 2004

(54) 5,6,7,8-TETRAHYDRONAPHTHALEN-2-YL 2,6-DIFLUOROHEPTATRIENOIC ACID DERIVATIVES HAVING SERUM GLUCOSE REDUCING ACTIVITY

(75) Inventors: Richard L. Beard, Newport Beach, CA (US); Haiqing Yuan, Irvine, CA (US); Yang-Dar Yuan, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/341,837

(22) Filed: Jan. 14, 2003

(51) Int. Cl.[7] .......................... C07C 69/76; C07C 62/06
(52) U.S. Cl. .......................... 560/56; 562/466; 514/532; 514/569
(58) Field of Search .......................... 560/56; 562/466; 514/532, 569

(56) References Cited

U.S. PATENT DOCUMENTS

| 5,455,265 A | 10/1995 | Chaudraratna |
| 5,721,103 A | 2/1998 | Boehm et al. |
| 5,801,253 A | 9/1998 | Klaus et al. |
| 6,114,533 A | 9/2000 | Vuligonda et al. |
| 6,326,397 B1 | 12/2001 | Bollag et al. |

FOREIGN PATENT DOCUMENTS

| WO | WO-93-11755 | 6/1993 |
| WO | WO-97-12853 | 4/1997 |
| WO | WO-01-19770 | 3/2001 |

OTHER PUBLICATIONS

Mangelsdorf et al. The Retinoid Receptors In: THe Retinoids pp.: 319–349 (1994).
Dawson et al. Chemistry and Biology of Synthetic Retinoids pp.: 324–356 (1990).
Mukherjee et al. Nature vol. 386 pp.: 407–410 (1997).
Heyman et al. Cell vol. 68 pp.: 397–406 (1992).
Allegretto et al. Journal of Biological Chemistry vol. 268 pp.: 26625–26633 (1993).
Cheng et al. Biochemical Pharmacology vol. 22 pp.: 3099–3108 (1973).

*Primary Examiner*—Paul J. Killos
(74) *Attorney, Agent, or Firm*—Gabor L. Szekeres; Robert J. Baran; Martin A. Voet

(57) ABSTRACT

Compounds of the formula

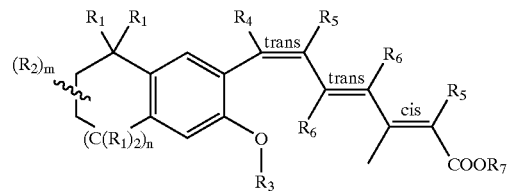

where the variables have the meaning defined in the specification are capable of reducing serum glucose levels in diabetic mammals without the undesirable side effect of reducing serum thyroxine levels.

24 Claims, No Drawings

5,6,7,8-TETRAHYDRONAPHTHALEN-2-YL 2,6-DIFLUOROHEPTATRIENOIC ACID DERIVATIVES HAVING SERUM GLUCOSE REDUCING ACTIVITY

BACKGROUND OF THE INVENTION

FIELD OF INVENTION

The present invention relates to compounds that have the property of reducing serum glucose and serum triglyceride levels in diabetic mammals without the undesirable properties of reducing serum thyroxine levels and transiently raising triglyceride levels. More particularly, the present invention relates to 5,6,7,8-tetrahydronaphthalen-2-yl 2,6-difluoroheptatrienoic acid derivatives having the above-noted biological property.

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$, and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356. The following further patents are of interest as background to the present invention: U.S. Pat. Nos. 5,721,103; 5,801,253; 6,326,397; PCT Publications WO 97/12853 and WO 01/19770.

Relatively recently it has become known that certain retinoid compounds are capable of reducing serum glucose levels in diabetic mammals. Mukherjee, R.; Davies, P. J.; Crombie, D. L. Bishoff, E. D.; Cesario, R. M.; Jow Hamann, L. G.; Boehm, M. F.; Mondon, C. E.; Nadzan, A. M.; Paterniti, J. R. Jr.; Heyman, R. A. Sensitization of Diabetic and Obese Mice to Insulin by Retinoid X Receptor Agonists. Nature 1997, 386(6623), 407–410. The compound (2E,4E,1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid, described in U.S. Pat. No. 6,114,533, has this property. A disadvantage of the prior art retinoid compounds that reduce serum glucose levels is that their administration usually also results in the pharmacologically undesirable reduction of serum thyroxine levels and a transient increase in serum triglyceride levels. The present invention is directed to novel compounds which do not have these undesirable side effects.

SUMMARY OF THE INVENTION

The present invention relates to compounds of Formula 1

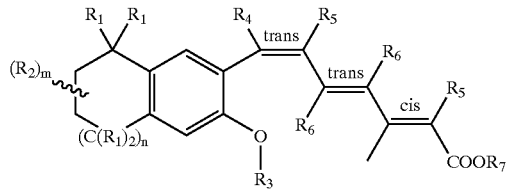

Formula 1 where m is an integer having the values of 0 to 4;

n is an integer having the values of 0 or 1;

$R_1$ is independently H, or alkyl of 1 to 6 carbons;

$R_2$ is independently H, alkyl of 1 to 6 carbons, F, Cl, Br or I;

$R_3$ is alkyl of 1 to 4 carbons, or $CH_2OR_8$, $R_4$ is alkyl of 1 to 3 carbons;

$R_5$ is independently F or Cl;

$R_6$ is H, F, or Cl, and $R_7$ is H, alkyl of 1 to 6 carbons, $CH_2OR$ or $CH_2OCOR_8$ where $R_8$ is alkyl of 1 to 3 carbons, or a pharmaceutically acceptable salt of said compound.

The present invention also relates to pharmaceutical compositions incorporating the compounds of Formula 1 and to methods of treatment of diabetic mammals with pharmaceutical compositions containing one or more compounds of Formula 1 to reduce serum glucose levels in said mammals. The present invention also relates to the methods of using the compounds of the invention to treat diseases and conditions which are responsive to treatment by retinoids.

DETAILED DESCRIPTION OF THE INVENTION

General Embodiments and Synthetic Methodology
Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. The compounds of the present invention have the specific orientations of substituents relative to the double bonds as is indicated in the name of the respective compound, and/or by specific showing in the structural formula of the orientation of the substituents relative to the respective double bonds.

Some of the compounds of the present invention may contain one or more chiral centers and therefore may exist in enantiomeric and diastereomeric forms. The scope of the present invention is intended to cover the trans and cis (E and Z) isomers as specifically shown and/or named, as well as pure enantiomers (optical isomers), diastereomers, mixtures of diastereomers and racemic mixtures of enantiomers.

Reaction Scheme 1 discloses a presently preferred synthetic route to compounds of the invention which are tetrahydronaphthalene derivatives (in Formula 1 the integer n=1). Although this synthetic route is general, the cis and/or trans isomerism of the compounds of the invention is indicated properly, the variable $R_5$ of Formula 1 is shown as fluoro (F) and the variable $R_6$ is shown as hydrogen (H), as in the preferred embodiments. However, based on the present disclosure and general knowledge in the art those having ordinary skill in synthetic methodology can readily modify the herein described reactions to obtain all compounds within the scope of Formula 1 including those where $R_5$ is chloro (Cl) and $R_6$ is fluoro or chloro.

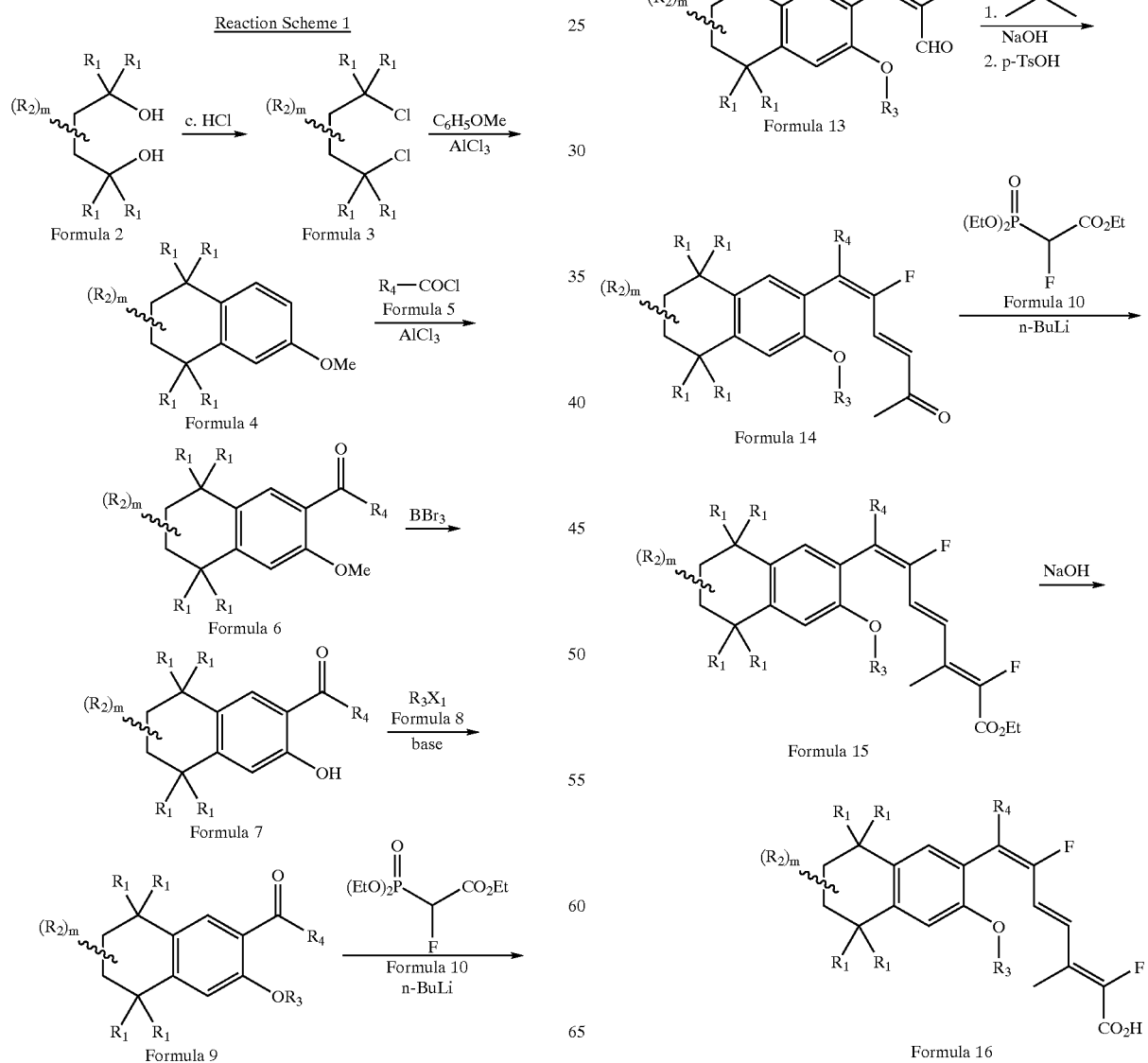

Referring now to Reaction Scheme 1 the starting material is a diol of Formula 2 that is already substituted with the $R_1$ and $R_2$ groups. Such diols are available commercially, or in accordance with the chemical scientific and patent literature, or by such modifications of known synthetic procedures that are readily apparent to those skilled in the art. An example for a compound in accordance with Formula 2 is 2,5-dimethyl-hexane-2,5-diol that is available commercially (Aldrich Chemical Co.) and serves as the starting material for the presently preferred compounds of the invention. The diol of Formula 2 is converted to the corresponding dichloro compound of Formula 3 by treatment with concentrated hydrochloric acid. The dichloro compound of Formula 3 is then subjected to a Friedel Crafts reaction with anisole (methoxybenzene) in the presence of aluminum chloride ($AlCl_3$) catalyst to yield a 3-methoxy-5,6,7,8-tetrahydronaphthalene derivative of Formula 4. The 3-methoxy-5,6,7,8-tetrahydronaphthalene derivative of Formula 4 is subjected to another Friedel Crafts reaction with an acid chloride of the formula $R_4$-COCl (Formula 55). The latter Friedel Crafts reaction is preferably conducted in an aprotic solvent, such as methylene chloride, in the presence of $AlCl_3$ catalyst. $R_4$ is defined as in connection with Formula 1. Examples for the acid chlorides used in this reaction are acetyl chloride, propionyl chloride and butyryl chloride. Acetyl chloride and propionyl chloride are used to prepare the presently preferred compounds of the invention.

The ketone compound of Formula 6 that is obtained in the Friedel Crafts reaction is then treated with boron tribromide ($BBr_3$) in an aprotic solvent, such as methylene chloride) to provide a 3-hydroxy-substituted 5,6,7,8-tetrahydronaphthalene derivative of Formula 7. The 3-hydroxy group of the compound of Formula 7 is then alkylated in the presence of base, with a reagent of the formula $R_3X_1$ where $R_3$ is defined as in connection with Formula 1 and $X_1$ is a leaving group, such as Cl, Br or I. Examples for the reagent $R_3X_1$ are methyl, ethyl, propyl halides (preferably iodides) and methoxymethyl chloride. The resulting 3-alkoxy-5,6,7,8-tetrahydronaphthalene derivative of Formula 9 is subjected to a Horner Emmons reaction with the reagent triethyl 2-fluoro-2-phosphonoacetate (available from Aldrich) to provide a fluoro substituted ester derivative of Formula 11. The Horner Emmons reaction per se is well known in the art, and is conducted in an aprotic solvent, such as heptane or tetrahydrofuran (THF) or mixtures of aprotic solvents, in the presence of strong base, such an n-butyl lithium or lithium diisopropylamide (LDA). The ester function of the compound of Formula 11 is first reduced to the primary alcohol level (Formula 12) by treatment with di-iso-butyl aluminum hydride (DIBAL-H), and is thereafter oxidized to the aldehyde stage (Formula 13) by treatment with N-methylmorpholine-N-oxide (NMO) in the presence of catalytic amounts of tetrapropylammonium peruthenate (TPAP). The aldehyde compound of Formula 13 is therafter subjected to base catalyzed (Aldol) condensation with acetone, and treated with acid to provide another ketone compound of Formula 14. The ketone of Formula 14 is subjected to still another Horner Emmons reaction with the reagent of Formula 10 to provide the 5,6,7,8-tetrahydronaphthalen-3-yl-heptatrienoic acid ester derivative of Formula 15. The compound of Formula 15 is within the scope of the present invention, and is also readily converted to the free acid (or salt thereof) of Formula 16 by saponification. The 5,6,7,8-tetrahydronaphthalen-3-yl-heptatrienoic acid derivative of Formula 16 is also within the scope of the present invention.

Reaction Scheme 2 illustrates a general route for the synthesis of compounds of the invention in which the variable n of Formula 1 is zero (0).

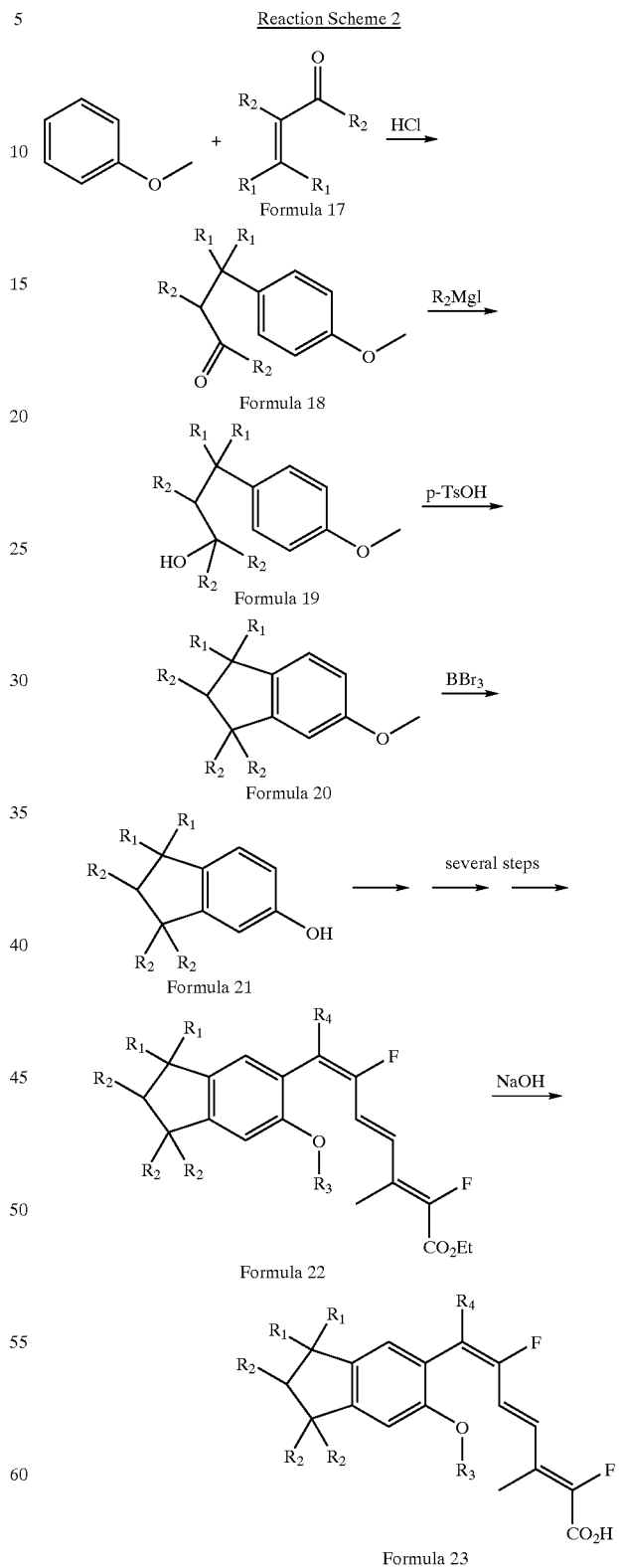

In accordance with this scheme anisole is reacted in a Friedel Crafts type reaction with an enone of Formula 17. The enone of Formula 17 includes the substituents $R_1$ and R$_2$, which are defined as in connection with Formula 1, except that the R$_1$ of Formula 7 in the preparation of these indane derivatives is not halogen. Preferably the R$_1$ and R$_2$ substituents in this scheme respectively represent methyl groups or hydrogen so as to give rise to indane derivatives of Formula 22 and of 23 that are substituted with two geminal dimethyl groups. The enones of Formula 17 are available commercially, or in accordance with the chemical scientific and patent literature, or by such modifications of known synthetic procedures that are readily apparent to those skilled in the art. An example for a compound in accordance with Formula 2 is 4-methyl-3-penten-2-one. Reaction of anisole with the enone of Formula 17 gives rise to the ketone compound of Formula 18. The ketone of Formula 18 is reacted with a Grignard reagent of the formula R$_2$MgI where the variable R$_2$ represents an alkyl group as defined in Formula 1. The resulting alcohol of Formula 19 is cyclized by treatment with acid to give the methoxy substituted indane derivative of Formula 20. The methoxy substituted indane derivative of Formula 20 is reacted with boron tribromide to remove the methoxy group and to yield the hydroxy substituted indane derivative of Formula 21. The compound of Formula 21 is subjected to a series of reaction analogous to the reaction described in Reaction Scheme 1 (starting with Formula 4), to provide the indane substituted heptatrienoic acid ester (Formula 22) and indane substitituted heptatrienoic acid (Formula 23) derivatives, both of which are compounds of the invention within the scope of Formula 1.

Specific Embodiments of the Compounds of the Invention

Referring now to Formula 1, the presently preferred compounds of the invention are tetrahydronaphthalene derivatives (n of Formula 1 represents the integer one (1)).

In the preferred compounds of the invention the variable R$_1$ represents alkyl groups of 1 to 3 carbons, and even more preferably methyl. Still more preferably the tetrahydronaphthalene group is substituted in the 5 and 8 positions by geminal dimethyl groups and still further substitution of the non-aromatic portion by additional R$_2$ groups is presently not preferred. The R$_3$ group of the preferred compounds is ethyl, n-propyl or methoxymethyl. The variable R$_4$ of the preferred compounds is methyl or ethyl, and R$_5$ is preferably fluoro (F). R$_6$ is preferably hydrogen, and R$_7$ is preferred as H, or alkyl of 1 to 3 carbons or methoxymethyl, or as a pharmaceutically acceptable salt of the carboxylic acid. Still more preferably R$_7$ is H (or a salt of the carboxylic acid) or ethyl.

The synthesis of the presently most preferred compounds of the invention is shown in Reaction Schemes 3, 4 and 5 and a detailed description of the experimental procedures for synthesizing these most preferred exemplary compounds is also provided below.

Reaction Scheme 3

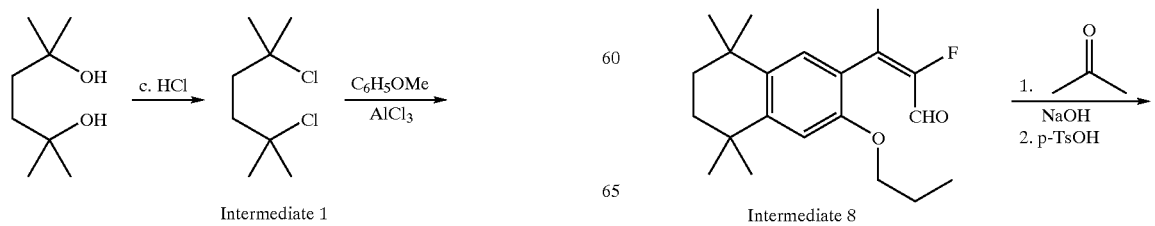

Intermediate 1

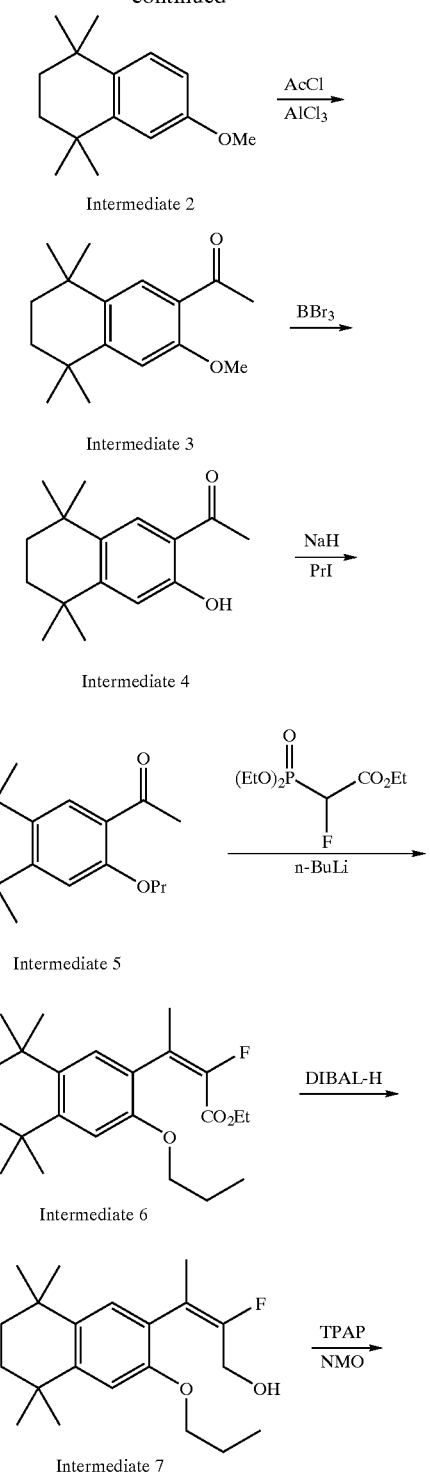

Intermediate 2

Intermediate 3

Intermediate 4

Intermediate 5

Intermediate 6

Intermediate 7

Intermediate 8

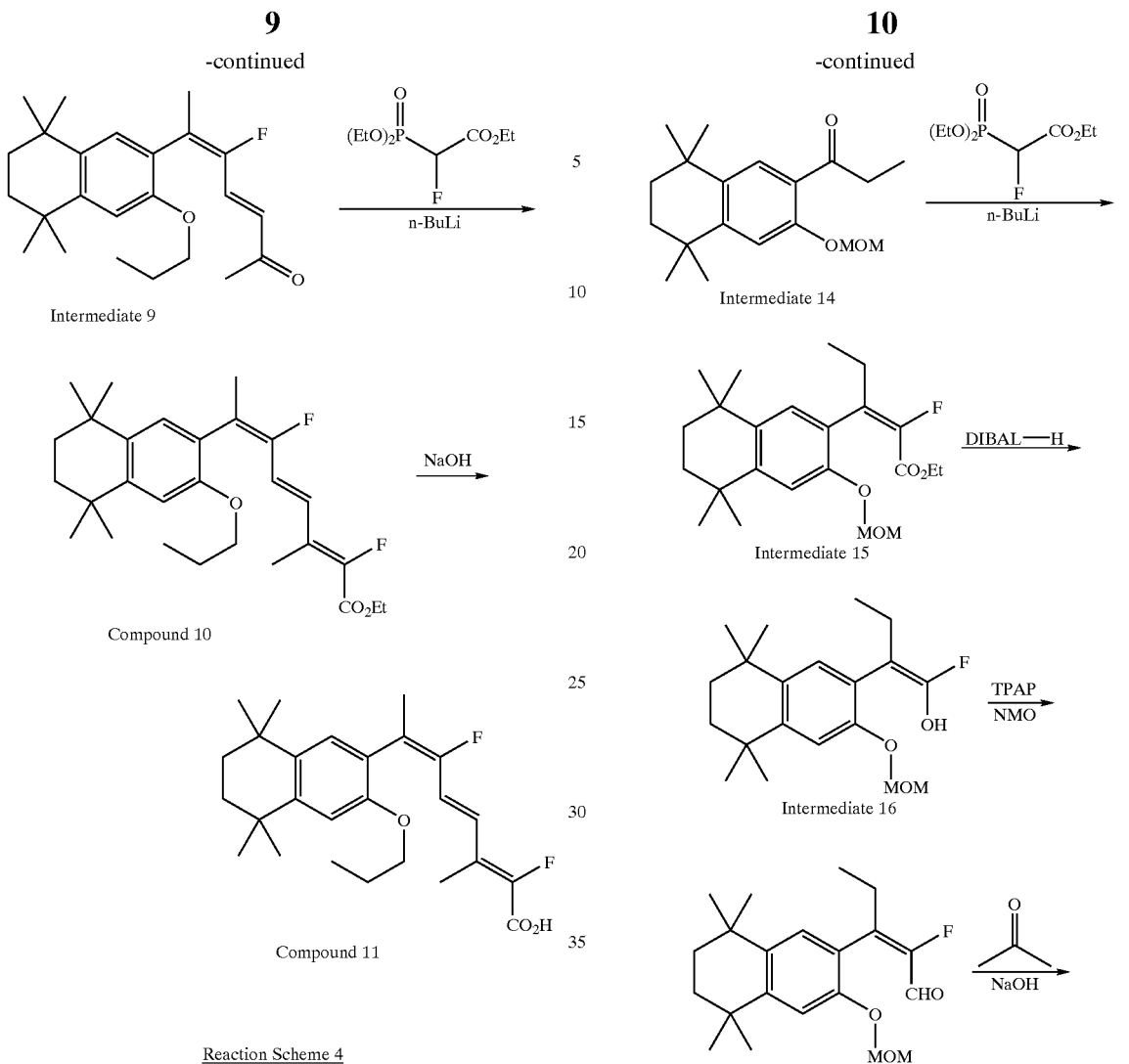

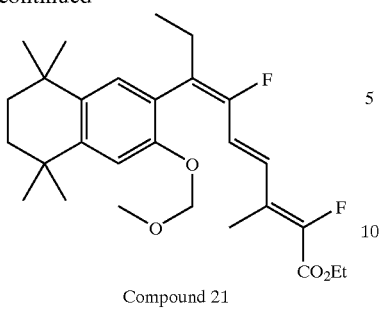

Compound 21

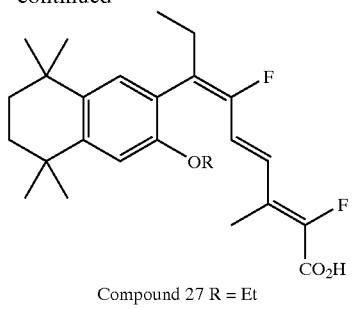

Compound 27 R = Et
Compound 28 R = Pr

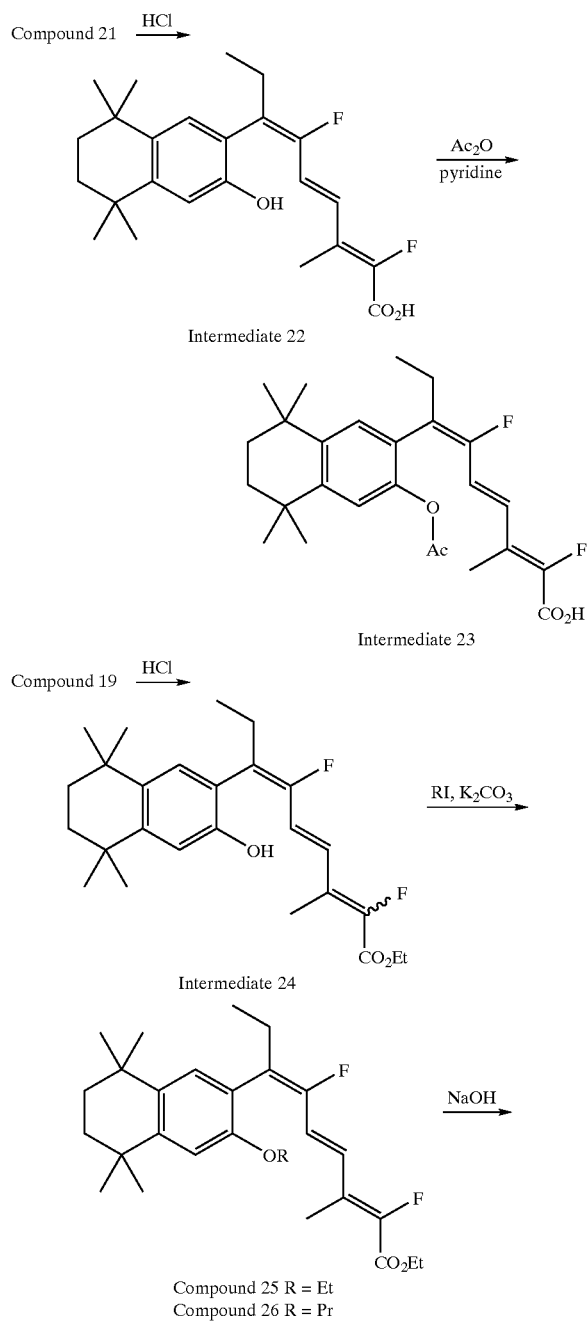

Experimental Procedures For Synthesizing the Exemplary Compounds of the Invention 2,5-Dichloro-2,5-dimethyl-hexane (Intermediate 1)

Concentrated HCl (1.2 L, 14.4 mol) was added to commercial 2,5-dimethyl-hexane-2,5-diol (202 g, 1.4 mol) and the slurry was stirred at ambient temperature for 1.5 h. The mixture was filtered. The filter cake was washed with water (×3), dissolved in $Et_2O$, washed successively with $H_2O$, $NaHCO_3$, and brine, dried over $Na_2SO_4$, and concentrated in vacuo. Recrystallization of the resulting solid from $Et_2O$ gave the title compound as white crystals (216 g, 85%).

$^1$H NMR (300 MHz, $CDCl_3$): δ1.60 (s, 12H), 1.95 (s, 4H).

6-Methoxy-1,1,4,4-tetramethyl-1,2,3,4-tetrahydro-naphthalene (Intermediate 2)

To a solution of 2,5-dichloro-2,5-dimethyl-hexane (Intermediate 1, 25.3 g, 0.14 mol) in anisole (60 mL, 0.55 mol) at 0° C. was added $AlCl_3$ (18.4 g, 0.14 mmol) portionwise. After stirring for 2 h at 0° C., the mixture was poured onto ice and extracted with hexane. The organic layer was washed with brine, dried over $Na_2SO_4$, and concentrated in vacuo. The excess anisole was removed by vacuum distillation and the title compound was obtained as a white solid upon cooling (30.5 g, 100%).

$^1$H NMR (300 MHz, $CDCl_3$): δ1.26 (s, 6H), 1.28 (s, 6H), 1.67 (s, 4H), 3.79 (s, 3H), 6.71 (dd, J=8.8, 2.9 Hz, 1H), 6.83 (d, J=2.9 Hz, 1H), 7.23 (d, J=8.8 Hz, 1H).

General Procedure A 1-(3-Methoxy-5,5,8,8-tetramethyl-5,6,7,8-tetrahydro-naphthalen-2-yl)-ethanone (Intermediate 3)

To a suspension of $AlCl_3$ (6.6 g, 49.6 mmol) in $CH_2Cl_2$ (225 mL) at 0° C. was added acetyl chloride (3.5 mL, 49.6 mmol) dropwise via syringe. To the resulting homogeneous light brown solution was added 6-methoxy-1,1,4,4-tetramethyl-1,2,3,4-tetrahydro-naphthalene (Intermediate 2, 9.0 g, 41.3 mmol) in $CH_2Cl_2$ (25 mL) via cannula. The mixture was then stirred at ambient temperature for 1 h, poured onto ice and extracted with $Et_2O$ (×2). The combined organic layer was washed with brine, dried over $Na_2SO_4$, and concentrated in vacuo to give the title compound as a white solid (10.7 g, 100%).

$^1$H NMR (300 MHz, $CDCl_3$): δ1.27 (s, 6H), 1.30 (s, 6H), 1.68 (s, 4H), 2.59 (s, 3H), 3.89 (s, 3H), 6.85 (s, 1H), 7.32 (s, 1H), 7.73 (s, 1H).

1-(3-Hydroxy-5,5,8,8-tetramethyl-5,6,7,8-tetrahydro-naphthalen-2-yl)-ethanone (Intermediate 4)

To a solution of 1-(3-methoxy-5,5,8,8-tetramethyl-5,6,7,8-tetrahydro-naphthalen-2-yl)-ethanone (Intermediate 3, 10.7 g, 41.2 mmol) in CH$_2$Cl$_2$ (500 mL) at 0° C. was added BBr$_3$ (49.5 mL, 1.0 M in CH$_2$Cl$_2$) via syringe pump over 10 min. The mixture was stirred at 0° C. for 2 h and was quenched with ice-H$_2$O and extracted with Et$_2$O (×3). The combined organic layer was washed with brine, dried over Na$_2$SO$_4$, and concentrated in vacuo. The residue was purified by flash column chromatography on silica gel (CH$_2$Cl$_2$) to give the title compound as a brown solid (7.6 g, 75%).

$^1$H NMR (300 MHz, CDCl$_3$): δ1.28 (s, 6H), 1.29 (s, 6H), 1.69 (s, 4H), 2.61 (s, 3H), 6.90 (s, 1H), 7.65 (s, 1H), 11.87 (s, 1H).

1-(5,5,8,8-tetramethyl-3-propoxy-5,6,7,8-tetrahydro-naphthalen-2-yl)-ethanone (Intermediate 5)

To a solution of 1-(3-hydroxy-5,5,8,8-tetramethyl-5,6,7,8-tetrahydro-naphthalen-2-yl)-ethanone (Intermediate 4, 6.4 g, 26 mmol) in DMF (100 mL) at 0° C. was added NaH (1.2 g, 60%, 31 mmol). After stirring for 30 min, PrI (3.0 mL, 31 mmol) was added. The reaction was stirred at 0° C. for 4 h, was quenched with aqueous NH$_4$Cl and extracted with Et$_2$O (×2). The combined organic layer was washed with brine, dried over Na$_2$SO$_4$, and concentrated in vacuo.

Recrystalization of the residue from Et$_2$O gave the title compound as a white solid (5.0 g, 67%).

$^1$H NMR (300 MHz, CDCl$_3$): δ1.07 (t, J=7.3 Hz, 3H), 1.26 (s, 6H), 1.28 (s, 6H), 1.86 (m, 2H) 1.66 (s, 4H), 2.61 (s, 3H), 3.99 (q, J=6.4 Hz, 2H), 6.81 (s, 1H), 7.73 (s, 1H).

General Procedure B

(E)-2-Fluoro-3-(5,5,8,8-tetramethyl-3-propoxy-5,6,7,8-tetrahydro-naphthalen-2-yl)-but-2-enoic acid ethyl ester (Intermediate 6)

To a solution of LDA (12.1 mL, 2.0 M in heptane/THF/ethylbenzene) in THF (10 mL) at −78° C. was added triethyl 2-fluoro-2-phosphonoacetate (5.0 g, 20.7 mmol) in THF (10 mL). The reaction flask was removed from dry ice cooling bath for 12 min and then re-cooled to −78° C. 1-(5,5,8,8-tetramethyl-3-propoxy-5,6,7,8-tetrahydro-naphthalen-2-yl)-ethanone (Intermediate 5, 1.98 g, 6.89 mmol) in THF (10 mL) was added and the reaction was allowed to warm up to ambient temperature over night. The reaction was quenched with aqueous NH$_4$Cl and extracted with Et$_2$O (×3). The combined organic layer was washed with brine, dried over Na$_2$SO$_4$, and concentrated in vacuo. The residue was purified by flash column chromatography on silica gel (3% EtOAc-hexane) to give a ~10:1 mixture of the title compound and its 2-Z isomer (2.2 g). The mixture was used directly in the next reaction.

General Procedure C

(E)-2-Fluoro-3-(5,5,8,8-tetramethyl-3-propoxy-5,6,7,8-tetrahydro-naphthalen-2-yl)-pent-2-en-1-ol (Intermediate 7)

To a solution of(E)-2-fluoro-3-(5,5,8,8-tetramethyl-3-propoxy-5,6,7,8-tetrahydro-naphthalen-2-yl)-but-2-enoic acid ethyl ester (Intermediate 6, 2.2 g, 5.85 mmol) in THF (50 mL) at −78° C. was added DIBAL-H (23.4 mL, 1.0 M in CH$_2$Cl$_2$, 23.4 mmol) over 10 min. After stirring at −78° C. for 3 h, the reaction was quenched with aqueous NH$_4$Cl followed by 1M HCl and was extracted with Et$_2$O (×3). The combined organic layer was washed with brine, dried over Na$_2$SO$_4$, and concentrated in vacuo. The residue was purified by flash column chromatography on silica gel (10% EtOAc-hexane) to give the title compound (1.02 g, 45% over 2 steps).

$^1$H NMR (500 MHz, CDCl$_3$): δ1.00 (t, J=7.3 Hz, 3H), 1.22 (s, 6H), 1.27 (2 s 6H), 1.65 (br s, 4H), 1.72–1.79 (m, 2H), 1.97 (d, J=3.4 Hz, 3H), 3.88 (t, J=5.9 Hz, 2H), 3.99 (d, J=22.9 Hz, 2H), 6.77 (s, 1H), 6.99 (s, 1H).

General Procedure D

(E)-2-Fluoro-3-(5,5,8,8-tetramethyl-3-propoxy-5,6,7,8-tetrahydro-naphthalen-2-yl)-but-2-enal (Intermediate 8)

A mixture of (E)-2-fluoro-3-(5,5,8,8-tetramethyl-3-propoxy-5,6,7,8-tetrahydro-naphthalen-2-yl)-pent-2-en-1-ol (Intermediate 7, 1.01 g, 3.04 mmol), NMO (0.89 g, 7.60 mmol), TPAP (catalytic amount), and 4 Å molecular sieves (200 mg) in CH$_2$Cl$_2$—CH$_3$CN (40 mL, 8 mL) was stirred at ambient temperature for 45 min. The mixture was loaded onto a pad of silica gel and eluted with 10% EtOAc-hexane to give the tide compound as a pale yellow solid (890 mg, 89%).

$^1$H NMR (300 MHz, CDCl$_3$): δ1.00 (t, J=7.3 Hz, 3H), 1.23 (s, 6H), 1.30 (s, 6H), 1.68 (br s, 4H), 1.76 (m, 2H), 2.24 (d, J=3.8 Hz, 3H), 3.91 (t, J=6.5 Hz 2H), 6.79 (s, 1H), 7.02 (s, 1H), 9.19 (d, J=19.6 Hz, 1H).

(3E, 5E)-5-Fluoro-6-(5,5,8,8-tetramethyl-3-propoxy-5,6,7,8-tetrahydro-naphthalen-2-yl)-hepta-3,5-dien-2-one (Intermediate 9)

To a solution of (E)-2-fluoro-3-(5,5,8,8-tetramethyl-3-propoxy-5,6,7,8-tetrahydro-naphthalen-2-yl)-but-2-enal (Intermediate 8, 208 mg, 0.63 mmol) in acetone (2 mL) was added 1M NaOH (2 mL) at 0° C. The mixture was stirred for 40 min, quenched with 2M H$_2$SO$_4$ (2 mL), and was stirred for 10 min. The mixture was then extracted with Et$_2$O (×3). The combined organic layer was washed successively with brine, NaHCO$_3$, brine, was dried over Na$_2$SO$_4$ and concentrated in vacuo. The residue was purified by flash column chromatography on silica gel (5%→10%→20% EtOAc-hexane) to give the title compound (35 mg) and the intermediate β-hydroxy ketone (173 mg), which was converted to the title compound using catalytic para-tolunesulfonic acid (PTSA) in refluxing benzene.

Total yield 197 mg, 85%.

$^1$H NMR (300 MHz, CDCl$_3$): δ1.00 (t, J=7.3 Hz, 3H), 1.24 (s, 6H), 1.30 (s, 6H), 1.68 (s, 4H), 1.70–1.82 (m, 2H), 2.16 (d, J=3.8 Hz, 3H), 2.17 (s, 3H), 3.89 (t, J=6.5 Hz, 2H), 6.36 (d, J=15.5 Hz, 1H), 6.78 (s, 1H), 6.94 (s, 1H), 6.96 (dd, J=27.0, 15.8 Hz, 1H).

(2Z,4E,6E)-2,6-Difluoro-3-methyl-7-(5,5,8,8-tetramethyl-3-propoxy-5,6,7,8-tetrahydro-naphthalen-2-yl)-octa-2,4,6-trienoic acid ethyl ester (Compound 10)

Following General Procedure B and using triethyl 2-fluoro-2-phosphonoacetate (0.3 mL, 1.44 mmol), THF (4 mL), n-BuLi (0.9 mL, 1.6 M in hexane, 1.44 mmol), (3E,5E)-5-fluoro-6-(5,5,8,8-tetramethyl-3-propoxy-5,6,7,8-tetrahydro-naphthalen-2-yl)-hepta-3,5-dien-2-one (Intermediate 9, 177 mg, 0.48 mmol) in THF (2 mL) at −78° C. for overnight, the title compound and its 2-E isomer were obtained by flash column chromatography on silica gel (3% EtOAc-hexane) as a ~1.4:1 mixture (222 mg). Further purification by HPLC (2.5% EtOAc-hexane) afforded the title compound as a clear oil (102 mg, 47%).

$^1$H NMR (300 MHz, CDCl$_3$): δ1.01 (t, J=7.5 Hz, 3H), 1.23 (s, 6H), 1.30 (s, 6H), 1.34 (t, J=6.9 Hz, 3H), 1.67 (br s, 4H), 1.78 (m, 2H), 2.05 (d, J=3.3 Hz, 3H), 2.13 (d, J=3.6 Hz,

3H), 3.90 (t, J=6.3 Hz, 2H), 4.28 (q, J=7.2 Hz, 2H), 6.39 (dd, J=26.4, 15.6 Hz, 1H), 6.78 (s, 1H), 6.97 (s, 1H), 7.00 (d, J=15.0 Hz, 1H).

General Procedure E

(2Z,4E,6E)-2,6-Difluoro-3-methyl-7-(5,5,8,8-tetramethyl-3-propoxy-5,6,7,8-tetrahydro-naphthalen-2-yl)-octa-2,4,6-trienoic acid (Compound 11)

To a solution of (2Z,4E,6E)-2,6-difluoro-3-methyl-7-(5,5,8,8-tetramethyl-3-propoxy-5,6,7,8-tetrahydro-naphthalen-2-yl)-octa-2,4,6-trienoic acid ethyl ester (Compound 10, 82 mg, 0.18 mmol) in EtOH (2 mL) was added 1M NaOH (1.0 mL). The mixture was heated to 60° C. for 2 h and was cooled to ambient temperature, acidified with 1M HCl, and extracted with EtOAc (×3). The combined organic layer was washed with brine, dried over $Na_2SO_4$, and concentrated in vacuo. The residue was purified by flash column chromatography on silica gel (50% EtOAc-hexane) to give the title compound as a pale yellow solid (56 mg, 73%).

$^1$H NMR (300 MHz, $CDCl_3$): δ1.02 (t, J=7.5 Hz, 3H), 1.23 (s, 6H), 1.31 (s, 6H), 1.68 (br s, 4H), 1.78 (m, 2H), 2.08 (d, J=3.3 Hz, 3H), 2.14 (d, J=3.9 Hz, 3H), 3.90 (t, J=6.3 Hz, 2H), 6.46 (dd, J=26.1, 15.9 Hz, 1H), 6.79 (s, 1H), 6.97 (s, 1H), 7.00 (d, J=15.0 Hz, 1H).

1-(3-Methoxy-5,5,8,8-tetramethyl-5,6,7,8-tetrahydro-naphthalen-2-yl)-propan-1-one (Intermediate 12)

Following General Procedure A and using $AlCl_3$ (3.7 g, 27.5 mmol), $CH_2Cl_2$ (40 mL), propionyl chloride (2.4 mL, 27.5 mmol), and 6-methoxy-1,1,4,4-tetramethyl-1,2,3,4-tetrahydro-naphthalene (Intermediate 2, 5.0 g, 22.9 mmol) in $CH_2Cl_2$ (10 mL) at ambient temperature for 1.5 h followed by recrystallization from $Et_2O$, the title compound was obtained as a white solid (5.4 g, 86%).

$^1$H NMR (500 MHz, $CDCl_3$): δ1.15 (t, J=7.3 Hz, 3H), 1.27 (s, 6H), 1.30 (s, 6H), 1.65–1.70 (m, 4H), 2.98 (q, J=7.3 Hz, 2H), 3.88 (s, 3H), 6.83 (s, 1H), 7.70 (s, 1H).

1-(3-Hydroxy-5,5,8,8-tetramethyl-5,6,7,8-tetrahydro-naphthalen-2-yl)-propan-1-one (Intermediate 13)

To a solution of 1-(3-methoxy-5,5,8,8-tetramethyl-5,6,7,8-tetrahydro-naphthalen-2-yl)-propan-1-one (Intermediate 12, 2.07 g, 7.9 mmol) in $CH_2Cl_2$ (40 mL) at 0° C. was added $BBr_3$ (8.9 mL, 1M in $CH_2Cl_2$ 8.9 mmol) dropwise. After 30 min, the reaction was quenched with ice-$H_2O$, and extracted with EtOAc. The organic layer was washed with brine, dried over $Na_2SO_4$, and concentrated in vacuo. The residue was purified by flash column chromatography on silica gel (2% EtOAc-hexane) to give the title compound as a white solid (2.6 g, 90%).

$^1$H NMR (300 MHz, $CDCl_3$): δ1.24 (t, J=7.3 Hz, 3H), 1.27 (s, 6H), 1.28 (s, 6H), 1.68 (s, 4H), 3.03 (q, J=7.3 Hz, 2H), 11.96 (s, 1H).

1-(3-Methoxymethoxy-5,5,8,8-tetramethyl-5,6,7,8-tetrahydro-naphthalen-2-yl)-propan-1-one (Intermediate 14)

To a solution of 1-(3-hydroxy-5,5,8,8-tetramethyl-5,6,7,8-tetrahydro-naphthalen-2-yl)-propan-1-one (Intermediate 13, 2.6 g, 10 mmol)) in i-$Pr_2$NEt (28 mL) was added chloromethylmethyl ether (4.8 mL, 63 mmol). The mixture was stirred at ambient temperature for overnight, was quenched with 1M HCl, and extracted with EtOAc (×3). The combined organic layer was washed with brine, dried over $MgSO_4$, and concentrated in vacuo. The residue was purified by flash column chromatography on silica gel (3% EtOAc-hexane) to give the title compound as a white solid (2.79 g, 92%).

$^1$H NMR (500 MHz, $CDCl_3$): δ1.16 (t, J=7.3 Hz, 3H), 1.26 (s, 6H), 1.27 (s, 6H), 1.64–1.69 (m, 4H), 2.99 (q, J=7.3 Hz, 2H), 3.50 (s, 3H), 5.22 (s, 2H), 7.06 (s, 1H), 7.65 (s, 1H).

(E)-2-Fluoro-3-(3-methoxymethoxy-5,5,8,8-tetramethyl-5,6,7,8-tetrahydro-naphthalen-2-yl)-pent-2-enoic acid ethyl ester (Intermediate 15)

Following General Procedure B and using triethyl 2-fluoro-2-phosphonoacetate (5.6 mL, 27.6 mmol), THF (50 mL), n-BuLi (17.3 mL, 1.6 M in hexane, 27.6 mmol), and 1-(3-methoxymethoxy-5,5,8,8-tetramethyl-5,6,7,8-tetrahydro-naphthalen-2-yl)-propan-1-one (Intermediate 14, 2.8 g, 9.2 mmol) in THF (10 mL), followed by flash column chromatography on silica gel (3% EtOAc-hexane), the title compound was obtained as a mixture containing minimal 2-Z isomer (3.3 g). The mixture was used directly in the next reaction.

(E)-2-Fluoro-3-(3-methoxymethoxy-5,5,8,8-tetramethyl-5,6,7,8-tetrahydro-naphthalen-2-yl)-pent-2-en-1-ol (Intermediate 16)

Following General Procedure C and using (E) 2-fluoro-3-(3-methoxymethoxy-5,5,8,8-tetramethyl-5,6,7,8-tetrahydro-naphthalen-2-yl)-pent-2-enoic acid ethyl ester (Intermediate 15, 3.3 g, 8.4 mmol), $CH_2Cl_2$ (50 mL), and DIBAL-H (33.6 mL, 1.0 M in THF, 33.6 mmol) followed by flash column chromatography on silica gel (10%→20% EtOAc-hexane), the title compound was obtained as a white solid (2.4 g, 75% over 2 steps).

$^1$H NMR (500 MHz, $CDCl_3$): δ0.94 (t, J=7.3 Hz, 3H), 1.23 (s, 6H), 1.27 (s, 6H), 1.66 (br s, 4H), 2.40–2.48 (m, 2H), 3.48 (s, 3H), 3.98 (d, J=21.5 Hz, 2H), 5.10 (s, 2H), 6.95 (s, 1H), 6.97 (s, 1H).

(E)-2-Fluoro-3-(3-methoxymethoxy-5,5,8,8-tetramethyl-5,6,7,8-tetrahydro-naphthalen-2-yl)-pent-2-enal (Intermediate 17)

Following General Procedure D and using (E)-2-fluoro-3-(3-methoxymethoxy-5,5,8,8-tetramethyl-5,6,7,8-tetrahydro-naphthalen-2-yl)-pent-2-en-1-ol (Intermediate 16, 1.69 g, 4.83 mmol), NMO (1.4 g, 12.1 mmol), TPAP (catalytic amount), and $CH_2Cl_2$ (5 mL) followed by flash column chromatography on silica gel (5% EtOAc-hexane) the title compound was obtained as a off-white solid (1.48 g, 88%).

$^1$H NMR (300 MHz, $CDCl_3$): δ1.04 (t, J=7.6 Hz, 3H), 1.23 (s, 6H), 1.29 (s, 6H), 1.68 (s, 4H), 2.64 (m, 2H), 3.43 (s, 3H), 5.13 (s, 2H), 7.00 (s, 1H), 7.05 (s, 1H), 9.15 (d, J=19.6 Hz, 1H).

(3E,5E)-5-Fluoro-6-(3-methoxymethoxy-5,5,8,8-tetramethyl-5,6,7,8-tetrahydro-naphthalen-2-yl)-octa-3,5-dien-2-one (Intermediate 18)

To a solution of (E)-2-fluoro-3-(3-methoxymethoxy-5,5,8,8-tetramethyl-5,6,7,8-tetrahydro-naphthalen-2-yl)-pent-2-enal (Intermediate 17, 880 mg, 2.5 mmol) in acetone (10 mL) was added 1M NaOH (7.5 mL) at 0° C. The mixture was stirred for 5 h, quenched with 2M $H_2SO_4$ (10 mL), and was stirred for 30 min. The mixture was then extracted with EtOAc (×3). The combined organic layer was washed successively with brine, NaHCO$_3$, was dried over MgSO$_4$ and concentrated in vacuo. The residue was purified by flash column chromatography on silica gel (5% EtOAc-hexane) to give the title compound as a yellow solid (930 mg, 95%).

$^1$H NMR (500 MHz, CDCl$_3$): δ0.99 (t, J=7.3 Hz, 3H), 1.24 (s, 6H), 1.30 (s, 6H), 1.68 (s, 4H), 2.17 (s, 3H), 2.44–2.76 (m, 2H), 3.43 (s, 3H), 5.11 (s, 2H), 6.38 (d, J=15.6 Hz, 1H), 6.88 (dd, J=26.9, 15.6 Hz, 1H), 6.91 (s, 1H), 7.02 (s, 1H).

Mixture of (2E,4E,6E)-2,6-difluoro-7-(3-methoxymethoxy-5,5,8,8-tetramethyl-5,6,7,8-tetrahydro-naphthalen-2-yl)-3-methyl-nona-2,4,6-trienoic acid ethyl ester and (2Z,4E,6E)-2,6-difluoro-7-(3-methoxymethoxy-5,5,8,8-tetramethyl-5,6,7,8-tetrahydro-naphthalen-2-yl)-3-methyl-nona-2,4,6-trienoic acid ethyl ester (Compound 19)

Following General Procedure B and using triethyl 2-fluoro-2-phosphonoacetate (1.3 mL, 6.2 mmol), THF (7 mL), n-BuLi (3.9 mL, 1.6 M in hexane, 6.2 mmol), and (3E,5E)-5-fluoro-6-(3-methoxymethoxy-5,5,8,8-tetramethyl-5,6,7,8-tetrahydro-naphthalen-2-yl)-octa-3,5-dien-2-one (Intermediate 18, 0.8 g, 2.1 mmol) in THF (3 mL) followed by flash column chromatography on silica gel (3% EtOAc-hexane), the title compound was obtained as a clear thick oil (2-E/Z isomer, 987 mg, 100%). Separation of the E/Z isomer by HPLC (5% EtOAc-hexane) afforded Compound 20 as a clear oil.

$^1$H NMR (300 MHz, CDCl$_3$): δ0.98 (t, J=7.6 Hz, 3H), 1.23 (s, 6H), 1.30 (s, 6H), 1.34 (t, J=7.0 Hz, 3H), 1.68 (s, 4H), 2.04 (d, J=3.2 Hz, 3H), 2.47 (m, 1H), 2.67 (m, 1H), 3.44 (s, 3H), 4.28 (q, J=7.03 Hz, 2H), 5.11 (s, 2H), 6.28 (dd, J=26.1, 15.8 Hz, 1H), 6.94 (s, 1H), 7.00 (dd, J=15.8, 1.8 Hz, 1H), 7.02 (s, 1H).

(2Z,4E,6E)-2,6-Difluoro-7-(3-methoxymethoxy-5,5,8,8-tetramethyl-5,6,7,8-tetrahydro-naphthalen-2-yl)-3-methyl-nona-2,4,6-trienoic acid (Compound 21)

Following General Procedure E and using (2Z,4E,6E)-2,6-difluoro-7-(3-methoxymethoxy-5,5,8,8-tetramethyl-5,6,7,8-tetrahydro-naphthalen-2-yl)-3-methyl-nona-2,4,6-trienoic acid ethyl ester (Compound 20, 314 mg, 0.66 mmol), 1M NaOH (2.0 mL) and EtOH (5 mL) at 40° C. for overnight followed by flash column chromatography on silica gel (10%→50% EtOAc-hexane), the title compound was obtained as a yellow solid (282 mg, 95%). $^1$H NMR (300 MHz, CDCl$_3$): δ0.98 (t, J=7.6 Hz, 3H), 1.23 (s, 6H), 1.29 (s, 6H), 1.67 (s, 4H), 2.06 (d, J=3.2 Hz, 3H), 2.47 (m, 1H), 2.68 (m, 1H), 3.44 (s, 3H), 5.12 (s, 2H), 6.35 (dd, J=26.1, 15.8 Hz, 1H), 6.94 (s, 1H), 7.01 (dd, J=15.8, 1.8 Hz, 1H), 7.02 (s, 1H).

(2Z,4E,6E)-2,6-Difluoro-7-(3-hydro-5,5,8,8-tetramethyl-5,6,7,8-tetrahydro-naphthalen-2-yl)-3-methyl-nona-2,4,6-trienoic acid (Intermediate 22)

To a solution of (2Z,4E,6E)-2,6-difluoro-7-(3-methoxymethoxy-5,5,8,8-tetramethyl-5,6,7,8-tetrahydro-naphthalen-2-yl)-3-methyl-nona-2,4,6-trienoic acid (Compound 21, 231 mg, 0.52 mmol) in i-PrOH (2 mL) and THF (2 mL) was added conc. HCl (1.0 mL). The mixture was stirred at ambient temperature for overnight and extracted with EtOAc (×3). The combined organic layer was washed with brine, dried over Na$_2$SO$_4$, and concentrated in vacuo. The residue was purified by flash column chromatography on silica gel (10%→50% EtOAc-hexane) to give the title compound as a yellow solid (186 mg, 89%).

$^1$H NMR (300 MHz, CDCl$_3$): δ1.00 (t, J=7.6 Hz, 3H), 1.23 (s, 6H), 1.28 (s, 6H), 1.67 (s, 4H), 2.01 (d, J=3.4 Hz, 3H), 2.56 (m, 2H), 4.64 (br s, 1H), 6.26 (dd, J=25.6, 15.6 Hz, 1H), 6.81 (s, 1H), 6.93 (s, 1H), 7.07 (d, J=15.6 Hz, 1H).

(2Z,4E,6E)-7-(3-Acetoxy-5,5,8,8-tetramethyl-5,6,7,8-tetrahydro-naphthalen-2-yl)-2,6difluoro-3-methyl-nona-2,4,6-trienoic acid (Intermediate 23)

To a solution of (2Z,4E,6E)-2,6-difluoro-7-(3-hydroxy-5,5,8,8-tetramethyl-5,6,7,8-tetrahydro-naphthalen-2-yl)-3-methyl-nona-2,4,6-trienoic acid (Intermediate 22, 108 mg, 0.27 mmol) in pyridine (2 mL) at 0° C. was added acetic anhydride (100 μL, 1.1 mmol). The mixture was stirred for 4 h while warmed to ambient temperature. The reaction was quenched with aqueous Na$_2$CO$_3$, stirred for 30 min, acidified with 1M HCl and extracted with EtOAc (×3). The combined organic layer was washed with brine, dried over MgSO$_4$, and concentrated in vacuo. The residue was purified by flash column chromatography on silica gel (10%→50% EtOAc-hexane) to give the title compound as a yellow solid (82 mg, 69%).

$^1$H NMR (300 MHz, CDCl$_3$): δ0.97 (t, J=7.6 Hz, 3H), 1.26 (s, 6H), 1.29 (s, 6H), 1.70 (s, 4H), 2.06 (d, J=3.4 Hz, 3H), 2.19 (s, 3H), 2.36 (m, 1H), 2.62 (m, 1H), 6.26 (dd, J=25.9, 15.8 Hz, 1H), 6.99 (s, 1H), 7.02 (d, J=15.8 Hz, 1H), 7.05 (s, 1H), 10.38 (br s, 1H).

(2Z,4E,6E)-2,6-Difluoro-7-(3-hydroxy-5,5,8,8-tetramethyl-5,6,7,8-tetrahydro-naphthalen-2-yl)-3-methyl-nona-2,4,6-trienoic acid ethyl ester (Intermediate 24)

To a solution of (2Z,4E,6E)-2,6-difluoro-7-(3-methoxymethoxy-5,5,8,8-tetramethyl-5,6,7,8-tetrahydro-naphthalen-2-yl)-3-methyl-nona-2,4,6-trienoic acid ethyl ester (Compound 19, 2-E/Z mixture, 387 mg, 0.81 mmol) in i-PrOH (2 mL) and THF (2 mL) was added conc. HCl (1.0 mL). The mixture was stirred at ambient temperature for overnight, extracted with EtOAc (×3). The combined organic layer was washed with brine, dried over Na$_2$SO$_4$, and concentrated in vacuo. The residue was purified by flash column chromatography on silica gel (5% EtOAc-hexane) to give the title compound as a 2-E/Z mixture (370 mg, 100%). This mixture was used directly for the next alkylation reaction.

General Procedure F (2Z,4E,6E)-7-(3-Ethoxy-5,5,8,8-tetramethyl-5,6,7,8-tetrahydro-naphthale-2-yl)-2,6-difluoro-3-methyl-nona-2,4,6-trienoic acid ethyl ester (Compound 25)

A mixture of 2,6-difluoro-7-(3-hydroxy-5,5,8,8-tetramethyl-5,6,7,8-tetrahydro-naphthalen-2-yl)-3-methyl-nona-2,4,6-trienoic acid ethyl ester (Intermediate 24, 2-E/Z mixture, 180 mg, 0.42 mmol), K$_2$CO$_3$ (290 mg, 2.1 mmol), and EtI (0.17 mL, 2.1 mmol) in acetone (2 mL) was stirred at ambient temperature for overnight. The reaction was diluted with EtOAc, washed with brine, dried over Na$_2$SO$_4$, and concentrated in vacuo. The residue was purified by flash column chromatography on silica gel (3% EtOAc-hexane) to give a mixture of the tide compound and its 2-E isomer. Further purification by HPLC (2.5% EtOAc-hexane) afforded the title compound as a clear syrup (82 mg, 42%).

$^1$H NMR (300 MHz, CDCl$_3$): δ0.98 (t, J=7.5 Hz, 3H), 1.22 (s, 6H), 1.29 (s, 6H), 1.34 (t, J=7.2 Hz, 3H), 1.36 (t, J=7.2 Hz, 3H), 1.67 (s, 4H), 2.03 (d, J=3.3 Hz, 3H) 2.51 (m, 1H), 2.62 (m, 1H), 4.00 (br q, J=6.7 Hz, 2H), 4.28 (q, J=7.2 Hz, 2H), 6.32 (dd, J=26.4, 16.2 Hz, 1H), 6.77 (s, 1H), 6.92 (s, 1H), 7.01 (dd, J=1.8 Hz, 1H).

(2Z,4E,6E)-2,6-Difluoro-3-methyl-7-(5,5,8,8-tetramethyl-3-propoxy-5,6,7,8-tetrahydro-naphthalen-2-yl)-nona-2,4,6-trienoic acid ethyl ester (Compound 26)

Following General Procedure F and using 2,6-difluoro-7-(3-hydroxy-5,5,8,8-tetramethyl-5,6,7,8-tetrahydro-naphthalen-2-yl)-3-methyl-nona-2,4,6-trienoic acid ethyl ester (Intermediate 24, 2-E/Z mixture, 180 mg, 0.42 mmol), $K_2CO_3$ (290 mg, 2.1 mmol), and PrI (0.21 mL, 2.1 mmol) in acetone (2 mL), followed by HPLC (2.5% EtOAc-hexane) separation of the 2-E/Z product mixture, the title compound was obtained as a clear syrup (80 mg, 41%).

$^1$H NMR (300 MHz, CDCl$_3$): δ0.98 (t, J=7.5 Hz, 3H), 1.00 (t, J=7.4 Hz, 3H), 1.23 (s, 6H), 1.31 (s, 6H), 1.34 (t, J=7.2 Hz, 3H), 1.68 (s,4H), 1.76 (m, 2H), 2.04 (d, J=3.3 Hz, 3H), 2.51 (m, 1H), 2.65 (m, 1H), 3.89 (m, 2H), 4.28 (q, J=7.2 Hz, 2H), 6.32 (dd, J=26.4, 15.9 Hz, 1H), 6.77 (s, 1H), 6.93 (s, 1H), 7.00 (dd, J=15.9, 1.8 Hz,1H).

(2Z,4E,6E)-7-(3-Ethoxy-5,5,8,8-tetramethyl-5,6,7,8-tetrahydro-naphthalen-2-yl)-2,6-difluoro-3-methyl-nona-2,4,6-trienoic acid (Compound 27)

Following General Procedure E and using (2Z,4E,6E)-7-(-3-ethoxy-5,5,8,8-tetramethyl-5,6,7,8-tetrahydro-naphthalen-2-yl)-2,6-difluoro-3-methyl-nona-2,4,6-trienoic acid ethyl ester (Compound 25, 81 mg, 0.18 mmol), 1M NaOH (0.53 mL), and EtOH (2 mL) at 40° C. for overnight followed by flash column chromatography on silica gel (10%→50% EtOAc-hexane), the title compound was obtained as a yellow solid (46 mg, 61%).

$^1$H NMR (500 MHz, CDCl$_3$): δ0.98 (t, J=7.5 Hz, 3H), 1.22 (s, 6H), 1.30 (s, 6H), 1.36 (t, J=6.8 Hz, 3H), 1.68 (s, 4H), 2.04 (d, J=3.0 Hz, 3H), 2.51 (m, 1H), 2.65 (m, 1H), 4.00 (m, 2H), 6.38 (dd, J=26.0, 16.0 Hz, 1H), 6.78 (s, 1H), 6.92 (s, 1H), 7.00 (d, J=15.5 Hz, 1H), 10.23 (br s, 1H).

(2Z,4E,6E)-2,6-Difluoro-3-methyl-7-(5,5,8,8-tetramethyl-3-propoxy-5,6,7,8-tetrahydro-naphthalen-2-yl)-nona-2,4,6-trienoic acid (Compound 28)

Following General Procedure E and using (2Z,4E,6E)-2,6-difluoro-3-methyl-7-(5,5,8,8-tetramethyl-3-propoxy-5,6,7,8-tetrahydro-naphthalen-2-yl)-nona-2,4,6-trienoic acid ethyl ester (Compound 26, 80 mg, 0.17 mmol), 1M NaOH (0.51 mL), and EtOH (2 mL) at 40° C. for overnight followed by flash colulmn chromatography on silica gel (10%→50% EtOAc-hexane), the title compound was obtained as a yellow solid (54 mg, 72%).

$^1$H NMR (500 MHz, CDCl$_3$): δ0.98 (t, J=7.5 Hz, 3H), 1.00 (t, J=7.4 Hz, 3H), 1.23 (s, 6H), 1.31 (s, 6H), 1.68 (s, 4H), 1.77 (m, 2H), 2.05 (d, J=3.0 Hz, 3H), 2.52 (m, 1H), 2.68 (m, 1H), 3.89 (m, 2H), 6.38 (dd, J=26.0, 16.0 Hz, 1H), 6.78 (s, 1H), 6.93 (s, 1H), 7.01 (d, J=16.0 Hz, 1H).

Biological Activity, Modes of Administration

It has been discovered in accordance with the present invention that compounds of this invention are capable of significantly reducing serum glucose levels and reducing or maintaining serum triglyceride levels in diabetic mammals, without the undesirable side effect of also reducing serum thyroxine levels, and thereby avoid causing undesirable hypothyroidism, and transiently raising triglyceride levels. It is noteworthy in this connection that the compounds of the invention are more efficacious as agonists of RXR$_\beta$ retinoid receptors than as agonists of RXR$_\alpha$, and RXR$_\gamma$ retinoid receptors. Although the concept of efficacy is well known in the arts of medicinal chemistry, pharmacology and related sciences it is briefly explained here as follows.

As is known efficacy and potency of a drug are related but nevertheless different concepts. The effect of a drug on an enzyme, receptor or other biological test model can be expressed in terms of results accomplished, such as, for example, the percentage of inhibition of an enzyme, or the activity attained on a receptor. IC$_{50}$ numbers express a concentration at which a drug inhibits 50% of the enzyme's activity. EC$_{50}$ numbers express concentration of the drug at which the drugs causes 50% activation of a receptor, the percentage of activity in this case being measured relative to a reference drug or agent which is considered to cause 100% of activity of the receptor. The smaller are the IC$_{50}$ or EC$_{50}$ numbers, thus showing concentrations at 50% activity, the more potent is considered the drug. Unlike potency, efficacy of a drug is not measured by the concentration at which the drug can cause 50% of an effect, but rather on the maximum effect that the drug can bring about at maximum concentration as compared to a standard compound determined to have full efficacy. Thus, when comparing two drugs, the first one may have a lesser IC$_{50}$ or EC$_{50}$ concentration in a given assay, but the first drug's maximum activity even at maximum concentration may be less than the maximum activity attained by the second drug. In such a case the first drug is considered more potent, but the second one more efficacious. Two drugs may also have substantially equal potency, but substantially different efficacy, and visa versa.

Table 1 below shows that in one or more of the below described assays the compounds of the present invention are more efficacious as agonists of RXR$_\beta$ retinoid receptors than as agonists of RXR$_\alpha$ and RXR$_\gamma$ retinoid receptors.

One such assay is a chimeric receptor transactivation assay which tests for agonist-like activity in the RARα RARβ and RARγ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO093/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in EC$_{50}$ numbers, as they are also in the chimeric receptor transactivation assay. The results of the ligand binding assay are expressed in K$_i$ numbers. (See Cheng et al. Biochemical Pharmacology Vol. 22 pp 3099–3108, expressly incorporated herein by reference.) Efficacy in a transactivation assay is expressed as a percentage of the maximum potency attained by the compound compared to a standard which, in this case, is the compound named (2E,4E,1'S,2'S)-3-methly-5-[2'-methyl-2'-(5,5,8,8-tetramethyl-5,6,7,8-tetrahydro-naphthalen-2-yl)-cyclopropyl]-penta-2,4-dienoic acid. This standard compound is described in U.S. Pat. No. 6,114,533.

Table 1 discloses the activity of certain exemplary compounds of the invention in the above-described receptor transactivation and binding assays. Particularly, the transactivation data pertaining to activation of the RAR receptors were obtained in the chimeric assay, and the transactivation data pertaining to the activation of RXR receptors were obtained in the holoreceptor assay. In a chimeric receptor transactivation assay the compounds were essentially inactive in activating $RAR_\alpha$, $RAR_\beta$ and $RAR_\gamma$ receptors.

1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid, that is approximately equally efficacious in activating the $RXR_\alpha$, $RXR_\beta$ and $RXR_\gamma$ subtypes.

An assay described below tests the effect of compounds of the invention on serum glucose, tryglyceride and thyroxine levels in female 9–10 weeks old db/db mice.

TABLE 1

| compound number | Structure | RAR Trans. $EC_{50}$ nM RAR Bind. $K_i$ nM | | | RXR Trans. $EC_{50}$ nM RXR Bind. $K_i$ nM | | |
|---|---|---|---|---|---|---|---|
| | | α | β | γ | α | β | γ |
| Standard compound | | NA >10k | NA >10k | NA >10k | 0.08 (100) 1 | 0.4 (100) 1 | 0.09 (100) 1 |
| Compound 11 | | 5 (12) 1800 | >1k (25) 1720 | 180 (28) 250 | 3 (7) 11 | 43 (24) 65 | NA ND |
| Compound 21 | | NA 260 | 170 (24) 590 | NA 940 | 9 (41) 12 | 91 (45) 60 | 8 (36) ND |
| Compound 27 | | NA 930 | 95 (14) 1.8k | NA 6.4k | 4 (30) 5 | 32 (43) 20 | 3 (23) ND |

In Table 1, NA stands for not active at all as an agonist and ND stands for not determined. The first row of numbers pertaining to each compound is the measured $EC_{50}$ number. The second row of numbers indicates efficacy as a percentage compared to the standard compound, (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. The third row of numbers pertaining to each compound is the binding $K_i$ number.

Table 1 shows Compounds 11, 21 and 27 of the invention are significantly more effective in activating the $RXR_\beta$ subtype (RXR is defined as "retinoid X receptor") than in activating $RXR_\alpha$ and $RXR_\gamma$ subtypes. For comparison to the $RXR_\beta$ selective compounds of the invention Table 1 also provides data for the prior art compound (2E, 4E, Description of Assay Female diabetic db/db (9–10 weeks old) mice were maintained on standard laboratory food and treated by oral gavage with vehicle (corn oil), standard compound (2E, 4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid (5 mg/kg) or the test compound (5–100 mg/kg, as described in Table 2) daily for seven days at 8:00 AM. Blood samples (70 μl) were taken by orbital bleeding at 11:00 AM on day 0 (pretreatment), day 3, and day 6. On day 7, a blood sample (700 μl) was taken at 11:00 AM and the animals were sacrificed. Glucose, triglyceride and thyroxine (T4) levels were determined on a Boehringer Manheim Hatachi Clinical Chemistry Analyzer using standard protocols provided by the manufacturer and reagents that were supplied in commercially available kits (glucose and T4; Boehringer Manheim; triglycerides: Roche Diagnostics). Seven animals were treated in each group. The results of the assays are summarized in Table 2.

Table 2 below shows the results of this assay for exemplary Compound 27.

TABLE 2

Glucose, Triglycerides, and Thyroxine (T4) in Female db/db mice (9–10 weeks old).

| Treatment (dose) | Glucose (mg/dl) | | | Triglycerides (mg/dl) | | T4 ($\mu$g/dL) Day 7 |
| --- | --- | --- | --- | --- | --- | --- |
| | Day 0 | Day 3, 3 h | Day 6, 3 h | Day 0 | Day 3, 3 h | |
| Vehicle (Corn oil) | 398 ± 94 | 423 ± 66 | 481 ± 63 | 157 ± 40 | 141 ± 32 | 3.7 ± 0.4 |
| Standard compound (5 mg/kg) | 356 ± 116 | 249 ± 57 | 239 ± 38 | 152 ± 39 | 137 ± 43 | 2.6 ± 0.6 |
| Compound 27 (50 mg/kg) | 384 ± 47 | 290 ± 80 | 225 ± 70 | 152 ± 27 | 106 ± 49 | 3.9 ± 0.9 |

As the data indicate, the selectively $RXR_\beta$ efficacious compounds of the invention not only cause significant decrease in serum glucose levels and maintain or reduce triglyceride levels in diabetic mammals, but in contrast with the prior art standard compound (2E,4E,1'S,2'S)-3-methyl-5-[2'-methyl-2'-(5,5,8,8-tetramethyl-5,6,7,8-tetrahydronaphthalen-2-yl)-cyclopropyl]-penta-2,4-dienoic acid do not have the undesirable side effect of reducing serum thyroxine levels.

Modes of Administration, Dosing

To treat diabetic mammals, including humans for the purpose of reducing serum glucose levels in said mammals a pharmaceutical composition containing one or more compound of the invention is administered to the mammal in daily doses in the range of 1 to 100 mg per kg body weight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as imnuunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pennsylvania. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

What is claimed is:

1. A compound of the formula

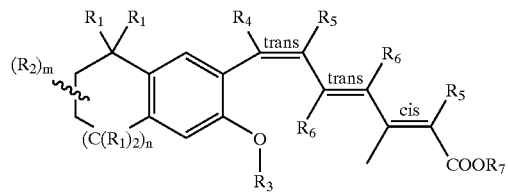

where m is an integer having the values of 0 to 4;
n is an integer having the values of 0 or 1;
$R_1$ is independently H, or alkyl of 1 to 6 carbons;
$R_2$ is independently H, alkyl of 1 to 6 carbons, F, Cl, Br or I;
$R_3$ is alkyl of 1 to 4 carbons, or $CH_2OR_8$;
$R_4$ is alkyl of 1 to 3 carbons;
$R_5$ is independently F or Cl;
$R_6$ is H, F, or Cl, and
$R_7$ is H, alkyl of 1 to 6 carbons, $CH_2OR_8$ or $OCH_2OCOR_8$ where $R_8$ is alkyl of 1 to 3 carbons, or a pharmaceutically acceptable salt of said compound.

2. A compound in accordance with claim 1 where n is 1.
3. A compound in accordance with claim 1 where n is 0.
4. A compound in accordance with claim 1 where $R_1$ is alkyl of 1 to 3 carbons.
5. A compound in accordance with claim 1 where $R_3$ is ethyl, n-propyl or methoxymethyl.
6. A compound in accordance with claim 1 where $R_4$ is methyl or ethyl.
7. A compound in accordance with claim 1 where $R_5$ is fluoro.
8. A compound of the formula

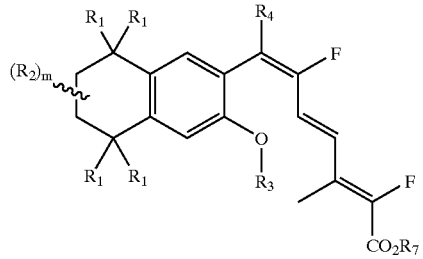

where m is an integer having the values of 0 to 4;
$R_1$ is independently alkyl of 1 to 3 carbons;
$R_2$ is independently H, alkyl of 1 to 3 carbons, F, Cl, Br or I;
$R_3$ is alkyl of 1 to 3 carbons, or $CH_2OR_8$;
$R_4$ is alkyl of 1 to 2 carbons, and
$R_7$ is H, alkyl of 1 to 6 carbons, $CH_2OR_8$ or $CH_2OCOR_8$ where $R_8$ is alkyl of 1 to 3 carbons, or a pharmaceutically acceptable salt of said compound.

9. A compound in accordance with claim 8 where m is zero (0).
10. A compound in accordance with claim 9 where $R_7$ is H, ethyl or methoxymethyl, or a pharmaceutically acceptable salt of said compound.
11. A compound of the formula

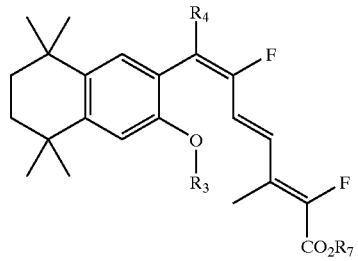

where $R_3$ is ethyl, n-propyl or methoxymethyl;
$R_4$ is methyl or ethyl, and
$R_7$ is H, ethyl or a pharmaceutically acceptable salt of said compound.

12. A compound in accordance with claim 11 where $R_4$ is methyl.
13. A compound in accordance with claim 12 where $R_3$ is n-propyl.
14. A compound in accordance with claim 13 where $R_7$ is H or a pharmaceutically acceptable salt of said compound.
15. A compound in accordance with claim 11 where $R_4$ is ethyl.
16. A compound in accordance with claim 15 where $R_3$ is n-propyl.
17. A compound in accordance with claim 16 where $R_7$ is H or a pharmaceutically acceptable salt of said compound.
18. A compound in accordance with claim 15 where $R_3$ is ethyl.
19. A compound in accordance with claim 18 where $R_7$ is H or a pharmaceutically acceptable salt of said compound.
20. A compound in accordance with claim 15 where $R_3$ is methoxymethyl.
21. A compound in accordance with claim 20 where $R_7$ is H or a pharmaceutically acceptable salt of said compound.
22. A process for administering to a diabetic mammal to reduce the serum glucose level of said mammal a compound of the formula

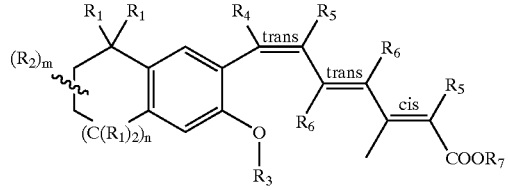

where m is an integer having the values of 0 to 4;
n is an integer having the values of 0 or 1;

R₁ is independently H, or alkyl of 1 to 6 carbons;
R₂ is independently H, alkyl of 1 to 6 carbons, F, Cl, Br or I;
R₃ is alkyl of 1 to 4 carbons, or CH₂OR₈;
R₄ is alkyl of 1 to 3 carbons;
R₅ is independently F or Cl;
R₆ is H, F, or Cl, and
R₇ is H, alkyl of 1 to 6 carbons, CH₂OR₈ or CH₂OCOR₈ where R₈ is alkyl of 1 to 3 carbons, or a pharmaceutically acceptable salt of said compound.

23. A process in accordance with claim 22 where the compound used in the process is in accordance with the formula

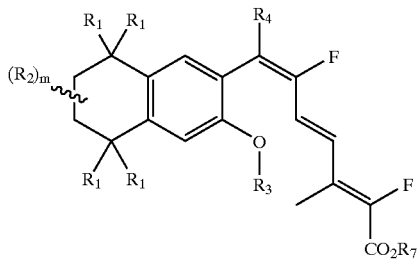

where
m is an integer having the values of 0 to 4;
R₁ is independently alkyl of 1 to 3 carbons;
R₂ is independently H, alkyl of 1 to 3 carbons, F, Cl, Br or I;
R₃ is alkyl of 1 to 3 carbons, or CH₂OR₈;
R₄ is alkyl of 1 to 2 carbons, and
R₇ is H, alkyl of 1 to 6 carbons, CH₂OR₈ or CH₂OCOR₈ where R₈ is alkyl of 1 to 3 carbons, or a pharmaceutically acceptable salt of said compound.

24. A process in accordance with claim 22 where the compound used in the process is in accordance with the formula

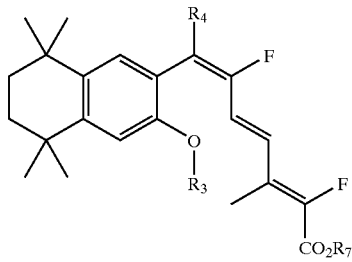

where
R₃ is ethyl, n-propyl or methoxymethyl;
R₄ is methyl or ethyl, and
R₇ is H, ethyl or a pharmaceutically acceptable salt of said compound.

* * * * *

UNITED STATES PATENT AND TRADEMARK OFFICE
CERTIFICATE OF CORRECTION

PATENT NO. : 6,759,547 B1
DATED : July 6, 2004
INVENTOR(S) : Beard et al.

It is certified that error appears in the above-identified patent and that said Letters Patent is hereby corrected as shown below:

Column 11,
Compound 21, " 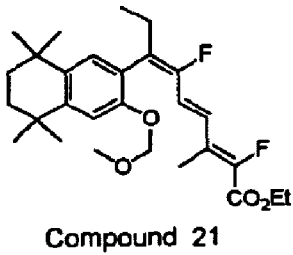 " should be -- 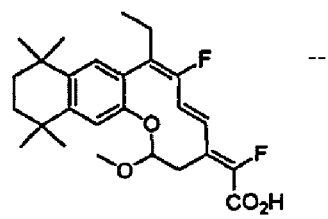 --

Column 20,
Line 35, "RARβ" should be -- RAR$_β$ --

Column 22,
Table 1, to the right of the standard compound ">10k >10k >10k" should be deleted and reinserted in the next line as -- >10k >10k >10k 1 1 1 --
Table 1, to the right of compound 11, "(12) (25) (28) (7) (24) (ND)" should be -- (12) (25) (28) (7) (24) --
Table 1, to the right of compound 11, "1800 1720 250 11 65" should be -- 1800 1720 250 11 65 ND --
Table 1, to the right of compound 11, "0" should be inserted below "1800."
Table 1, to the right of compound 21, "260" and "940" should be deleted from "260 (24) 940 (41) (45) (36)"
Table 1, to the right of compound 21, "590 12 60 ND" should be -- 260 590 940 12 60 ND --
Table 1, to the right of compound 27, "930 (14) 6.4k (30) (43) (23)" should be -- (14) (30) (43) (23) --
Table 1, to the right of compound 27, "1.8k 5 20 ND" should be -- 930 1.8k 6.4k 5 20 ND --

Signed and Sealed this

Twenty-eighth Day of December, 2004

JON W. DUDAS
*Director of the United States Patent and Trademark Office*

Disclaimer

6,759,547—Richard L. Beard, Newport Beach, CA (US); Haiqing Yuan, Irvine, CA (US); Yang-Dar Yuan, Irvine, CA (US); Roshantha A. Chandraratna, Laguna Hills, CA (US). 5,6,7,8-TETRAHYDRONAPHTHALEN-2-YL 2,6-DIFLUOROHEPTATRIENOIC ACID DERIVATIVES HAVING SERUM GLUCOSE REDUCING ACTIVITY. Patent dated July 6, 2004. Disclaimer filed August 8, 2011, by the assignee, Allergan, Inc., Irvine, CA (US).

Hereby disclaims all of the claims 1-24 of said patent.

*(Official Gazette November 22, 2011)*